US009408903B2

(12) United States Patent
MacAdam

(10) Patent No.: US 9,408,903 B2
(45) Date of Patent: Aug. 9, 2016

(54) VACCINATION METHOD EMPLOYING GENETICALLY STABLE ATTENUATED POLIOVIRUSES COMPRISING MULTIPLE MUTATIONS IN DOMAIN V OF THE 5' NONCODING REGION

(71) Applicant: The Secretary of State for Health, London (GB)

(72) Inventor: Andrew MacAdam, Potters Bar (GB)

(73) Assignee: The Secretary of State for Health, London (GB)

( * ) Notice: Subject to any disclaimer, the term of this patent is extended or adjusted under 35 U.S.C. 154(b) by 0 days.

(21) Appl. No.: 14/053,426

(22) Filed: Oct. 14, 2013

(65) Prior Publication Data

US 2014/0112952 A1 Apr. 24, 2014

Related U.S. Application Data

(63) Continuation of application No. 12/377,041, filed as application No. PCT/GB2007/003065 on Aug. 10, 2007, now Pat. No. 8,557,252.

(30) Foreign Application Priority Data

Aug. 10, 2006 (GB) .................................. 0615933.9

(51) Int. Cl.
*C12N 7/00* (2006.01)
*A61K 39/13* (2006.01)
*A61K 39/12* (2006.01)
*A61K 39/00* (2006.01)

(52) U.S. Cl.
CPC ................. *A61K 39/13* (2013.01); *A61K 39/12* (2013.01); *C12N 7/00* (2013.01); *A61K 2039/5254* (2013.01); *C12N 2770/32634* (2013.01); *C12N 2770/32661* (2013.01)

(58) Field of Classification Search
CPC ..................... A61K 39/13; C12N 7/00; C12N 2770/32661; C12N 2770/32634
See application file for complete search history.

(56) References Cited

U.S. PATENT DOCUMENTS

2013/0344108 A1  12/2013  MacAdam

FOREIGN PATENT DOCUMENTS

| EP | 0 383 433 A1 | 8/1990 |
|---|---|---|
| WO | 98/41619 A1 | 9/1998 |
| WO | 0007622 A1 | 2/2000 |
| WO | 2012090000 A1 | 7/2012 |

OTHER PUBLICATIONS

Rowe, A., et al., 2000, Coding changes in the poliovirus protease 2A compensate for 5'NCR domain V disruptions in a cell-specific manner, Virol. 269:284-293.*

Dragunsky, E. M., et al., 2004, Evaluation of immunogenicity and protective properties of inactivated poliovirus vaccines: a new surrogate method for predicting vaccine efficacy, J. Infect. Dis. 190:1404-1412.*
Combelas, N., et al., 2011, Recombination between poliovirus and coxsackie A viruses of species C: a model of viral genetic plasticity and emergence, Viruses 3:1460-1484.*
Almond, J., et al., "Approaches to the Construction of New Candidate Poliovirus Type 3 Vaccine Strains," Developments in Biological Standardization 78:161-169, 1993.
Girard, M., et al., "Potential Use of Poliovirus as a Vector," Biologicals 21(4):371-377, Dec. 1993.
International Search Report mailed Apr. 4, 2012, issued in related International Application No. PCT/GB2011/001779, filed Dec. 29, 2011, 3 pages.
International Preliminary Report on Patentability and Written Opinion mailed Jul. 2, 2013, issued in related International Application No. PCT/GB2011/001779, filed Dec. 29, 2011, 7 pages.
Chumakov, K., et al., "Inactivated Vaccines Based on Alternatives to Wild-Type Seed Virus," Developments in Biologicals (Basel) 105:171-177, 2001.
Combelas, N., et al., "Recombination Between Poliovirus and Coxsackie A Viruses of Species C: A Model of Viral Genetic Plasticity and Emergence," Viruses 3(8):1460-1484, Aug. 2011.
Dragunsky, E., et al., "Transgenic Mice as an Alternative to Monkeys for Neurovirulence Testing of Live Oral Poliovirus Vaccine: Validation by a WHO Collaborative Study," Bulletin of the World Health Organization 81(4):251-260, May 2003.
Evans, D.M., et al., "Increased Neurovirulence Associated With a Single Nucleotide Change in a Noncoding Region of the Sabin Type 3 Poliovaccine Genome," Nature 314(6011):548-550, Apr. 1985.
Georgescu, M.M., et al., "Mapping of Mutations Contributing to the Temperature Sensitivity of the Sabin 1 Vaccine Strain of Poliovirus," Journal of Virology 69(9):5278-5286, Sep. 1995.
Gutiérrez, A.L., et al., "Attenuating Mutations in the Poliovirus 5' Untranslated Region Alter Its Interaction With Polypyrimidine Tract-Binding Protein," Journal of Virology 71(5):3826-3833, May 1997.
Holland, J.J., et al., "RNA Virus Populations as Quasispecies," in J.J. Holland (ed.), "Genetic Diversity of RNA Viruses: Current Topics in Microbiology and Immunology," Springer, Berlin, 1992, vol. 176, Chap. 1, pp. 1-20.
La Monica, N., et al., "Mapping of Sequences Required for Mouse Neurovirulence of Poliovirus Type 2 Lansing," Journal of Virology 57(2):515-525, Feb. 1986.
MacAdam, A.J., et al., "The 5' Noncoding Region and Virulence of Poliovirus Vaccine Strains," Trends in Microbiology 2(11):449-454, Nov. 1994.
MacAdam, A.J., et al., "The 5' Noncoding Region of the Type 2 Poliovirus Vaccine Strain Contains Determinants of Attenuation and Temperature Sensitivity," Virology 181(2):451-458, Apr. 1991.
MacAdam, A.J., et al., "Correlation of RNA Secondary Structure and Attenuation of Sabin Vaccine Strains of Poliovirus in Tissue Culture," Virology 189(2):415-422, Aug. 1992.

(Continued)

*Primary Examiner* — Jeffrey Parkin
(74) *Attorney, Agent, or Firm* — Christensen O'Connor Johnson Kindness PLLC

(57) ABSTRACT

The invention provides an attenuated poliovirus which does not have a base pair mismatch in stem (a) or (b) of domain V of the 5' non-coding region of its genome, wherein at least seven of the base pairs in stems (a) and (b) are U-A or A-U base pairs.

10 Claims, 10 Drawing Sheets

(56) References Cited

OTHER PUBLICATIONS

MacAdam, A.J., et al., "Live-Attenuated Strains of Improved Genetic Stability," Developments in Biologicals (Basel) 105:179-187,2001.
MacAdam, A.J., et al., "Rational Design of Genetically Stable, Live-Attenuated Poliovirus Vaccines of All Three Serotypes: Relevance to Poliomyelitis Eradication," Journal of Virology 80(17):8653-8663, Sep. 2006.

Nomoto, A., et al., "Complete Nucleotide Sequence of the Attenuated Poliovirus Sabin 1 Strain Genome," Proceedings of the National Academy of Sciences of the USA (PNAS) 79(19):5793-5797, Oct. 1982.

Nomoto, A., et al., "Study of Virulence of Poliovirus Type 1 Using in Vitro Modified Viruses," in M.A. Brinton and R.R. Rueckert (eds.), "Positive Strand RNA Viruses: Proceedings of a Symposium Held in Keystone, Colorado, Apr. 20-26, 1986 (UCLA Symposia on Molecular Cell Biology," Alan R. Liss Inc., New York, pp. 437-452, 1987.

Skinner, M.A., et al., "New Model for the Secondary Structure of the 5' Non-Coding RNA of Poliovirus Is Supported by Biochemical and Genetic Data That Also Show That RNA Secondary Structure Is Important in Neurovirulence," Journal of Molecular Biology 207(2):379-392, May 1989.
Stanway, G., et al., "Comparison of the Complete Nucleotide Sequences of the Genomes of the Neurovirulent Poliovirus P3/Leon/37 and Its Attenuated Sabin Vaccine Derivative P3/Leon 12a1b," Proceedings of the National Academy of Sciences of the USA (PNAS) 81(5):1539-1543, Mar. 1984.
Vignuzzi, M., et al., "Engineering Attenuated Virus Vaccines by Controlling Replication Fidelity," Nature Medicine 14(21):154-161, Feb. 2008.
Vignuzzi, M., et al., "Quasispecies Diversity Determines Pathogenesis Through Cooperative Interactions in a Viral Population," Nature 439(7074):344-348, Jan. 2006.
International Search Report mailed Nov. 28, 2007, issued in corresponding International Application No. PCT/GB2007/003065, filed Aug. 10, 2007.
Written Opinion mailed Nov. 28, 2007, issued in corresponding International Application No. PCT/GB2007/003065, published Feb. 10. 2009.
International Preliminary Report on Patentability mailed Feb. 10, 2009, issued during the prosecution of International Application No. PCT/GB2007/003065, filed Aug. 10, 2007.

* cited by examiner

Fig. 1

Sabin 3

| Virus | Sequence of domain V | | | | | | | | |
|---|---|---|---|---|---|---|---|---|---|
| | | Stem a | | | | Stem b | | | |
| | 471 | | 473 | 477 | | | | | 483 |
| Sabin 3 | U | U | C...C | | C | A | U | G | G | A |
| | A | G | G...G | | G | U | G | C | C | U |
| | 538 | | 536 | 534 | | | | | 528 |
| | | Stem a | | | | Stem b | | | |
| | 468 | | 470 | 474 | | | | | 480 |
| Sabin 2 | U | C | C...C | | C | A | C | G | G | A |
| | A | G | G...G | | G | U | G | U | C | U |
| | 535 | | 533 | 531 | | | | | 525 |
| | | Stem a | | | | Stem b | | | |
| | 468 | | 470 | 474 | | | | | 480 |
| Sabin 1 | U | C | C...C | | C | U | C | G | G | G |
| | A | G | G...G | | G | U | G | C | C | U |
| | | | 533 | 531 | | | | | |
| | | Stem a | | | | Stem b | | | |
| Consensus | U | C | C...C | | C | U | C | G | G | G |
| | A | G | G...G | | G | U | G | C | C | U |

Bold Conserved base-pair
*Italic* Type-specific nucleotide

Fig. 2

VACCINATION METHOD EMPLOYING GENETICALLY STABLE ATTENUATED POLIOVIRUSES COMPRISING MULTIPLE MUTATIONS IN DOMAIN V OF THE 5' NONCODING REGION

CROSS-REFERENCES TO RELATED APPLICATIONS

This application is a continuation of U.S. patent application Ser. No. 12/377,041, filed Feb. 24, 2009, now U.S. Pat. No. 8,557,252, which is a national phase filing under 35 U.S.C. §371 of PCT International Application Serial No. PCT/GB2007/003065, filed Aug. 10, 2007, which claims priority to GB Patent Application Serial No. 0615933.9, filed Aug. 10, 2006, all of which applications are incorporated by reference herein in their entirety.

STATEMENT REGARDING SEQUENCE LISTING

The sequence listing associated with this application is provided in text format in lieu of a paper copy and is hereby incorporated by reference into the specification. The name of the text file containing the sequence listing is 43094_SEQUENCE_Final_2013-10-10.txt. The text file is 2 KB; was created on Oct. 10, 2013, and is being submitted via EFS-Web with the filing of the specification.

FIELD OF THE INVENTION

This invention relates to attenuated polioviruses, to their preparation and to vaccines containing them. More specifically, the invention relates to polioviruses which are attenuated and genetically stabilised by the introduction of defined mutations into their genomes. These polioviruses are particularly useful as inactivated poliovaccine seeds.

BACKGROUND

The live attenuated poliovirus vaccines developed by Sabin in the 1950s have found great use throughout the world. Vaccine strains derived from each of the three poliovirus serotypes, known as Sabin types 1, 2 and 3, were prepared by passage of wild-type viruses in cell cultures and whole animals until attenuated strains were obtained. These attenuated viruses are substantially less able to cause poliomyelitis in humans than the original wild-type strains. They are administered orally and replicate in the gut to induce a protective immune response.

Although the live oral poliovirus vaccines are generally regarded as safe, their use is associated with a small incidence of paralysis in vaccines. This is most often associated with type 2 and 3 serotypes and rarely, if ever, with type 1. Efforts have, therefore, been made to develop improved type 2 and type 3 vaccines which would be at least comparable in safety to the excellent type 1 strain.

The Sabin vaccine strains were developed by essentially empirical procedures. The genetic basis of their attenuation is not completely understood. Over the past several years, however, scientists have employed a number of molecular biological techniques in an attempt to elucidate the mechanism by which the neurovirulence of these vaccine strains is reduced. Most of the work has concentrated on serotypes 1 and 3. For both of these the complete nucleotide sequences of the vaccine strains have been compared with those of their neurovirulent progenitors.

In the case of poliovirus type 1, the vaccine strain differs from its progenitor at 47 positions in the 7441 base genome (Nomoto et al., Proc. Natl. Acad. Sci. USA 79:5793-5797, 1982). All of these are simple point mutations and 21 of them give rise to amino acid changes in virus-coded proteins. Although several mutations are thought to contribute to the attenuation phenotype of the vaccine strain, direct evidence has been presented that the mutation of A-G at position 480 in the 5' non-coding region of the genome has a marked attenuating effect on the virus (Nomoto et al., UCLA Symp. Mol. Cell. Biol., New Series, 54 (Eds M. A. Brinton and R. R. Rueckert):437-452, New York: Alan R. Liss Inc., 1987)).

Analogous studies on poliovirus type 3 reveal just 10 nucleotide sequence differences in the 7432 base genome between the vaccine and its progenitor strain (Stanway et al., Proc. Natl. Acad. Sci. USA 81:1539-1543, 1984). Just three of these give rise to amino acid substitutions in virus-encoded proteins. The positions of bases in the 5' non-coding region of the genome of type 3 poliovirus are numbered herein according to the numbering system of Stanway et al., 1984.

The construction of defined recombinants between the type 3 Sabin vaccine strain and its progenitor strain has allowed the identification of the mutations which contribute to the attenuation phenotype. One of these is at position 2034 and causes a serine to phenylalanine change in virus protein VP3.

The other mutation of interest is C (progenitor) to U (vaccine strain) at position 472 in the 5' non-coding region of the genome. This 472 U mutation has been observed to revert to the progenitor (wild-type) 472 C rapidly upon replication of the virus in the human gut (Evans et al., Nature 314:548-550, 1985). This reversion is associated with an increase in neurovirulence. C at position 472 has also been shown to be essential for growth of a mouse/human polio recombinant virus in the mouse brain (La Monica et al., J. Virol. 57:515-525, 1986). More recently, it has been observed that A changes to G at position 481 in poliovirus type 2, again upon replication of the virus in the gut of vaccines (Macadam et al., Virology 181:451-458, 1991).

A model for the secondary structure of the 5' non-coding region of the genome of poliovirus type 3 Leon strain has previously been proposed (Skinner et al., J. Mol. Biol. 207: 379-392, 1989). As concerns domain V (nucleotides 471-538), bases at positions 471-473 and 477-483 are paired with bases at positions 538-536 and 534-528 respectively as follows:

```
       471           477       483
    . . . U C C . . . C C A U G G A . . .

. . . A G G . . . G G U G C C U . . .
       538           534       528
```

For convenience, the paired regions are termed stem (a) (471-473/538-536) and stem (b) (477-483/534-528). Previously, we found that a type 3 poliovirus with the base pair 472-537 reversed, i.e. 472 G and 537 C, is attenuated. Further, this attenuated virus had a slightly lower $LD_{50}$ value than the corresponding poliovirus which only had the mutation C to G at position 472 but which retained the wild-type G at position 537. Attenuated polioviruses in which a base pair of stem (a) or stem (b) of domain V is reversed are disclosed in EP-A-0383433. However, subsequent experiments showed that the type 3 poliovirus in which the 472-537 base pair is reversed is not as attenuated as the type 3 Sabin vaccine strain.

We have also reported previously the production of attenuated polioviruses which have substantially the same attenuation as, or greater attenuation than, the Sabin vaccine strain (so that they are safe to use) but which are much more stable genetically. These attenuated polioviruses do not have a U-G base pair or other base pair mismatch in stem (a) or (b) of domain V of the 5' non-coding region of the poliovirus genome. (A departure from Watson-Crick base pairing is considered to be a mismatch.) More specifically, we prepared type 3 polioviruses which contained the following U-A base pairs:

(a) S15: U-A at 472-537, U-A at 480-531 and U-A at 481-530; or (b) S16: U-A at 472-537, U-A at 480-531 and A-U at 482-529.

Under conditions which rapidly selected neurovirulent variants of Sabin 3, the attenuation phenotypes of these poliovirus strains were stable (WO98/41619).

As a result of the success of the global polio eradication programme the proportion of cases attributable to vaccine-derived strains has increased dramatically and will continue to do so until live virus vaccination ceases. Partly in response to this, many developed countries have already switched to inactivated poliovaccines (IPV) which are currently produced from wild strains. When wild-type polio is eradicated wild-type strains will require high levels of biological containment, which may not be easy to reconcile with the production scales required for IPV, making the use of attenuated vaccine strains for IPV manufacture attractive, though it has been argued that both wild and attenuated strains ultimately present the same containment issues.

There remains a need for poliovirus strains that are non-infectious for humans at exposure levels potentially encountered in vaccine production facilities. This would significantly reduce the likelihood of escape into the environment and the consequences of escape would be negligible even after live virus vaccination has ceased. Such strains may be grown under containment levels that are not prohibitive for vaccine manufacturers.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

We have now designed and constructed poliovirus strains that may solve the safety and containment problems of current IPV seeds. These strains grew to titres as high as those of Sabin strains in cell culture at 33° C. but infectivity at 37° C. was significantly reduced, and by more than one million-fold in one case. This type 3 strain appeared completely attenuated, causing no clinical symptoms at all when inoculated intraspinally into TgPVR mice at a dose 5,000 times higher than the dose of Sabin 3 required to paralyse 50% of mice. The strains are also designed to be genetically stable using an approach involving manipulation of RNA secondary structure in domain V of the 5' non-coding region. Sequences of capsid proteins are unchanged in these strains so immunogenicity of inactivated preparations is expected to be unimpaired.

Accordingly, the present invention provides an attenuated poliovirus which does not have a U-G base pair or a base pair mismatch in stem (a) or (b) of domain V of the 5' non-coding region of the poliovirus genome and wherein at least seven of the base pairs in stems (a) and (b) are U-A or A-U base pairs. Preferably, at least five of the base pairs in stem (b) are U-A or A-U base pairs. The poliovirus may be a type 1, type 2 or type 3 poliovirus. An attenuated type 3 poliovirus in which the 5' non-coding region of the genome of the poliovirus contains a U-A base pair at positions 472-537, 478-533, 480-531 and 481-530 is preferred. Particularly, preferred are attenuated polioviruses which additionally contain an A-U base pair at position 482-529 or 477-534, or both. "Attenuated" means attenuated with respect to the wild-type poliovirus which is the progenitor of the relevant Sabin vaccine strains (each strain has its own progenitor) and also with respect to the relevant Sabin vaccine strain. Overall, the virus must be sufficiently attenuated to be non-infectious for humans.

The present invention also provides:
- a poliovirus of the invention which is inactivated;
- a poliovirus of the invention for use in a vaccine;
- a vaccine comprising a poliovirus of the invention and a pharmaceutically acceptable carrier or diluent;
- use of a poliovirus of the invention as an inactivated poliovaccine seed; and
- a method for preparing an inactivated poliovaccine, comprising:
  (i) growing an attenuated poliovirus according to the invention;
  (ii) inactivating said poliovirus; and
  (iii) formulating said inactivated poliovirus with a pharmaceutically acceptable carrier or diluent.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

Figure 1:
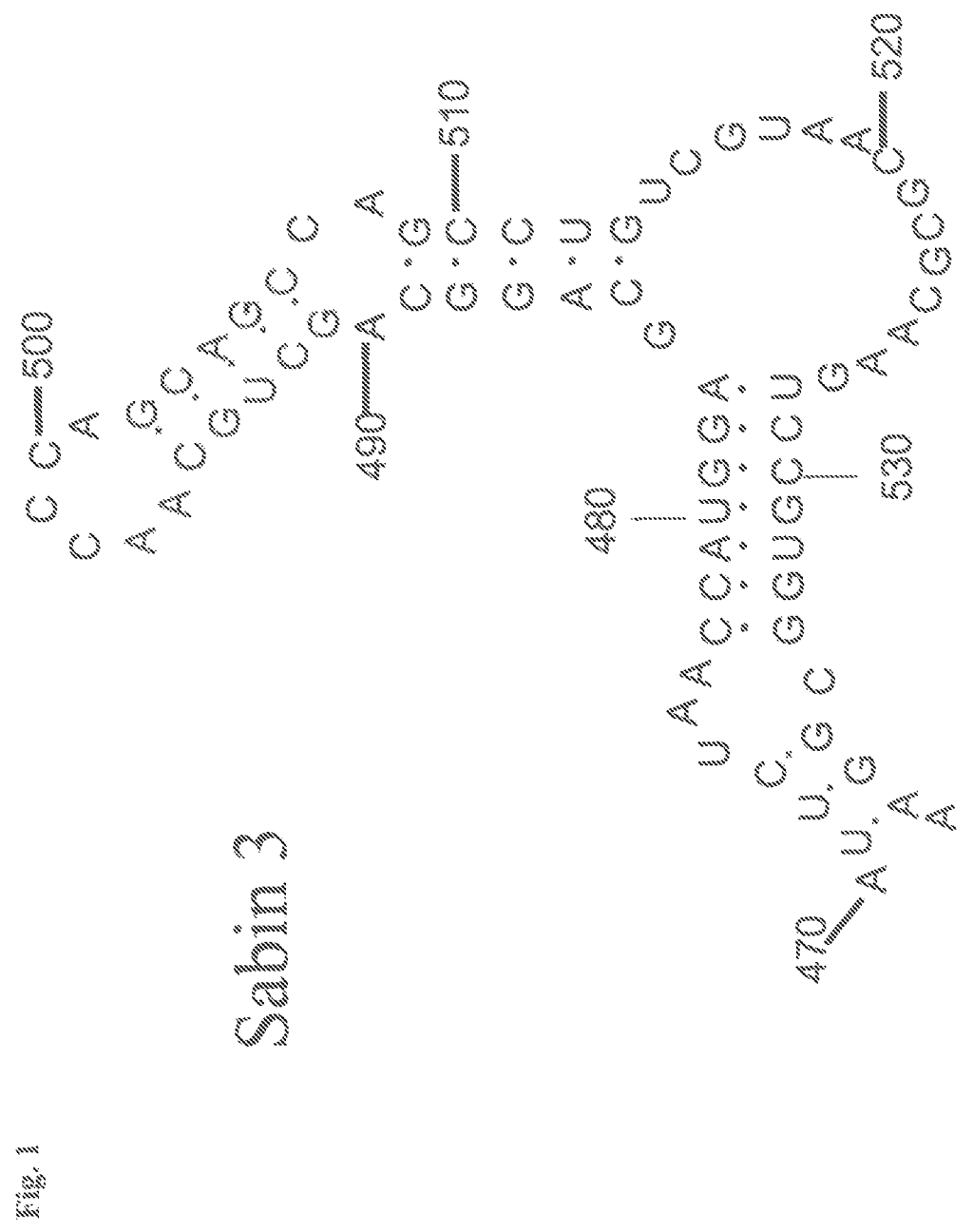

FIG. 1 shows the predicted RNA secondary structure of domain V (nucleotides 471-538) of the type 3 Sabin strain (SEQ ID NO: 1). The base-paired stem region from 471-473 and 536-538 is stem (a) and the base-paired stem region from 477-483 and 528-534 is stem (b).

FIG. 2 shows the sequence of stems (a) and (b) of domain V of the Sabin vaccine strains of each type of poliovirus. Domain V of a type 3 poliovirus extends from positions 471-538. Domain V of a type 2 or a type 1 poliovirus extends from positions 468-535.

DETAILED DESCRIPTION

Figure 3:
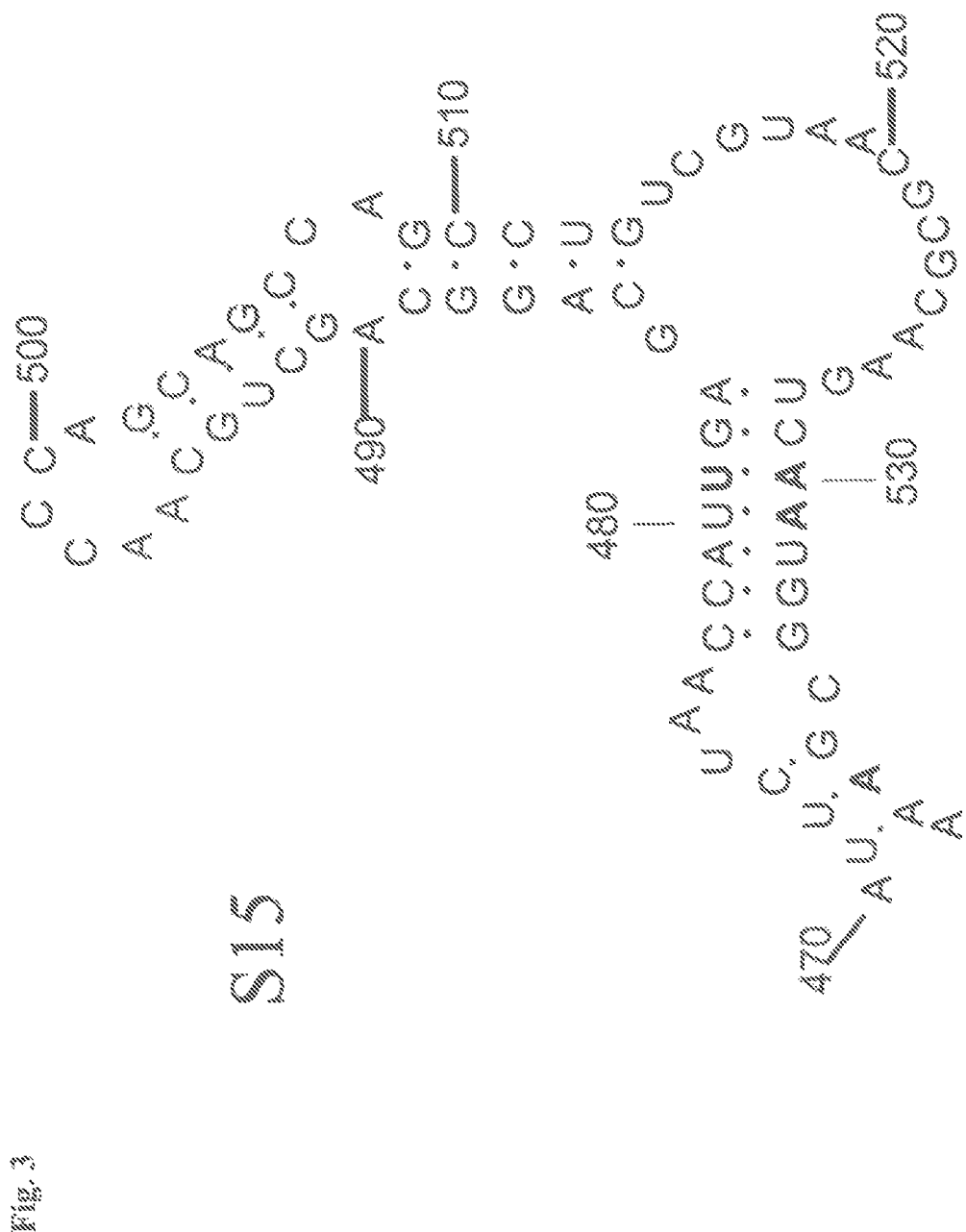
FIG. 3 shows the predicted RNA secondary structure of domain V (nucleotides 471-538) of the prior art attenuated poliovirus strain designated S15 (SEQ ID NO: 2).

The invention provides an attenuated poliovirus which does not have a base pair mismatch in stem (a) or (b) of domain V of the 5' non-coding region of its genome, wherein at least seven of the base pairs in stems (a) and (b) are U-A or A-U base pairs. Preferably, at least five, such as six or seven, of the base pairs in stem (b) are U-A or A-U base pairs. Preferably, at least two of the base pairs in stem (a) are U-A or A-U base pairs, for example, three of the base pairs in stem (a) maybe U-A or A-U base pairs.

Attenuated polioviruses of the invention have been modified so that stems (a) and (b) of the domain V do not contain a U-G base pair or other base pair mismatch such as the U-U mismatch in the type 1 Sabin vaccine strain. Preferably, stems (c) and (d) also do not contain a U-G base pair or other base pair mismatch. An alternative A-U or U-A base pair is provided in place of the pair mismatch. Thus, a U-A base pair is preferably present at positions 472-537 and 480-531 of domain V of a type 3 poliovirus, and at position 527-478 of a type 2 poliovirus, replacing U-G base pairs (refer to FIG. 2).

In addition, stems (a) and/or (b) of domain V have been modified to replace two or more G-C or C-G base pairs with A-U or U-A base pairs. Stem (b) of Sabin 3 contains C-G base pairs at positions 477-534 and 478-533 and G-C base pairs at positions 481-530 and 482-529. Two, three or four of these base pairs are replaced with U-A, A-U or a mixture of A-U and U-A base pairs. Stem (a) may also be modified to replace the C-G base pair at position 473-536 with an A-U or U-A base pair, preferably an A-U base pair.

In one embodiment, an attenuated poliovirus according to the invention comprises domain V of the 5' non-coding region of poliovirus type 3 in which a U-A base pair is present at position 472-537 in stem (a) and at positions 478-533, 480-531 and 481-530 in stem (b). A further A-U base pair may be present at position 482-529 in stem (b) and/or at position 477-534 in stem (b).

Type 1 and type 2 polio viruses can be correspondingly derived from the sequence of stems (a) and (b) of the wild-type neurovirulent type 1 and type 2 polioviruses. All strains are preferably Sabin. Alternatively, the entire domain V from a type 3 poliovirus of the invention may replace the entire domain V from a type 1 or type 2 poliovirus. For example, the entire 5' non-coding region from a type 3 poliovirus of the invention may replace the entire 5' non-coding region from a type 1 or type 2 poliovirus.

The mutations in the polioviruses of the invention attenuate the virulence of the virus and genetically stabilise existing live attenuated vaccine virus strains, thereby making them less likely to revert to virulence. These mutations also make the virus safe to produce at a lower containment level than the containment level required for the wild-type viruses used to produce inactivated poliovaccines and the containment level that would be necessary to grow the existing attenuated Sabin strains for inactivated poliovaccine production.

An attenuated poliovirus according to any one of the preceding claims may be inactivated.

The present invention provides a process for the preparation of an attenuated poliovirus of the invention, which process comprises:

(i) introducing the or each desired mutation by site-directed mutagenesis into a sub-cloned region, which includes the or each position it is wished to mutate, of a DNA copy of a poliovirus genome;

(ii) reintroducing the thus modified region into a complete copy DNA from which the region was derived; and (iii) obtaining live virus from the copy DNA thus obtained.

A mutation can thus be introduced into a strain of a poliovirus, normally a Sabin strain, by site-directed mutagenesis of a copy DNA corresponding to the genomic RNA of a poliovirus. This may be achieved by sub-cloning an appropriate region from an infectious DNA copy of a poliovirus genome into the single strand DNA of a bacteriophage such as M13.

After the introduction of the or each mutation, the modified sub-cloned copy DNAs are reintroduced into the complete copy DNA from which they were derived. Live virus is recovered from the mutated full length copy DNA by production of a positive sense RNA typically using a T7 promoter to direct transcription in vitro (Van der Werf et al., Proc. Natl. Acad. Sci. USA 83:2330-2334, 1986).

The recovered RNA may be applied to tissue cultures using standard techniques (Koch, Curro Top. Microbiol. Immunol. 61:89-138, 1973). After two to three days of incubation, virus can be recovered from the supernatant of the tissue culture. The level of neurovirulence and thus of attenuation of the modified virus may then be compared with that of the unmodified virus using a standard $LD_{50}$ test in mice or the above-mentioned WHO-approved vaccine safety test in monkeys.

Attenuation due to weakening of domain V has also been shown to correlate approximately with temperature sensitivity in BGM cells (Macadam et al., Virology 181:451-458, 1991) or in L20B cells (as described for CM-1 cells in Macadam et al., Virology 189:415-422, 1992). The temperature sensitivity of modified virus can thus be determined as a preliminary screen to determine the level of attenuation expected. This can be expressed as the temperature (T) at which the number of plaque forming using (pfu) is reduced by a power of 10 (1.0 $\log_{10}$) from the number obtained at, for example, 33° C. or 35° C. in the same cells. The lower the value of T, the greater the degree of attenuation.

The attenuated polioviruses can be used as live vaccines. They may, therefore, be formulated as pharmaceutical compositions further comprising a pharmaceutically acceptable carrier or diluent. Any carrier or diluent conventionally used in live vaccine preparations may be employed. For example, the attenuated polioviruses can be stabilised in 1M aqueous $MgCl_2$ and administered as a mixture of the three serotypes.

The attenuated polioviruses can, therefore, be used to prevent poliomyelitis in a human patient. For this purpose, they may be administered orally, as a nasal spray, or parenterally, for example by subcutaneous or intramuscular injection. A dose corresponding to the amount administered for a conventional Sabin vaccine strain, such as from $10^4$-$10^6$ $TCID_{50}$, may be administered.

The attenuated polioviruses may be used as inactivated-poliovaccine (IPV) seeds. Accordingly, the present invention provides an inactivated attenuated poliovirus of the invention and the use of a poliovirus according to the invention as an inactivated poliovaccine (IPV) seed. Also provided by the invention is a method for preparing an inactivated poliovaccine, comprising:
 (i) growing an attenuated poliovirus according to the invention;
 (ii) inactivating said poliovirus; and
 (iii) formulating said inactivated poliovirus with a pharmaceutically acceptable carrier or diluent.

The poliovirus may be inactivated by any suitable method. Typically, methods used to inactivate wild-type poliovirus in the currently used IPVs are employed. For example, the poliovirus may be inactivated by formaldehyde treatment.

Attenuated poliovirus strains of the invention may be inactivated and combined with a pharmaceutically acceptable carrier or diluent. Any carrier or diluent conventionally used in inactivated virus preparations, such as IPV preparations, may be employed. The IPV preparation may comprise inactivated type 1, type 2 and type 3 polioviruses.

The attenuated inactivated polioviruses of the invention can therefore be used to vaccinate against poliomyelitis in a human patient. For this purpose, they may be administered by any suitable route, such as parenterally. Parenteral administration may be by subcutaneous or intramuscular injection. A dose corresponding to the amount administered for a conventional IPV, such as 8 to 40 D antigen units, may be administered.

The following Examples illustrate the invention.

EXAMPLES

Construction and Recovery of Site-Directed Mutants

S15, S17, S18 and S19 are derivatives of the type 3 oral poliovaccine strain Sabin 3. Derivation of the Sabin 3 cDNA clone and construction of S15 have been described previously (Westrop et al., J. Virol. 63:1338-1344, 1989; WO 98/419619). Mutated nucleotides are shown in bold in FIGS. 3 to 6, otherwise sequences are identical to Sabin 3. Replacement of C-G base-pairs by U-A or A-U base-pairs progressively lowers the thermodynamic stability of domain V; removal of all U-G base-pairs makes the structure genetically stable as any single mutation would then weaken the relevant base-pair. Two simultaneous mutations would be required to strengthen the structure as this could only be achieved by changing a U-A base-pair to a C-G (or G-C) base-pair.

Figure 4:
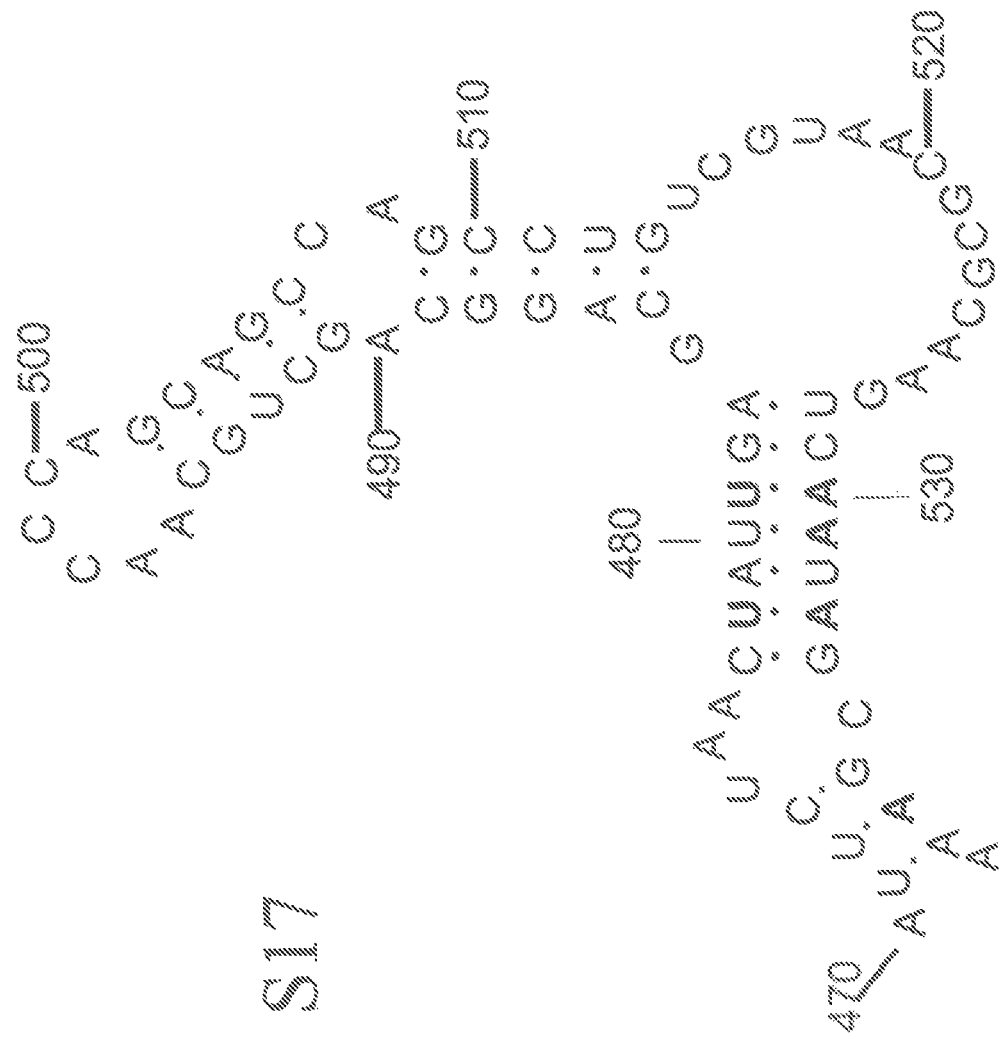
FIG. 4 shows the predicted RNA secondary structure of domain V (nucleotides 471-538) of the attenuated strain of the invention designated S17 (SEQ ID NO: 3).
Figure 5:
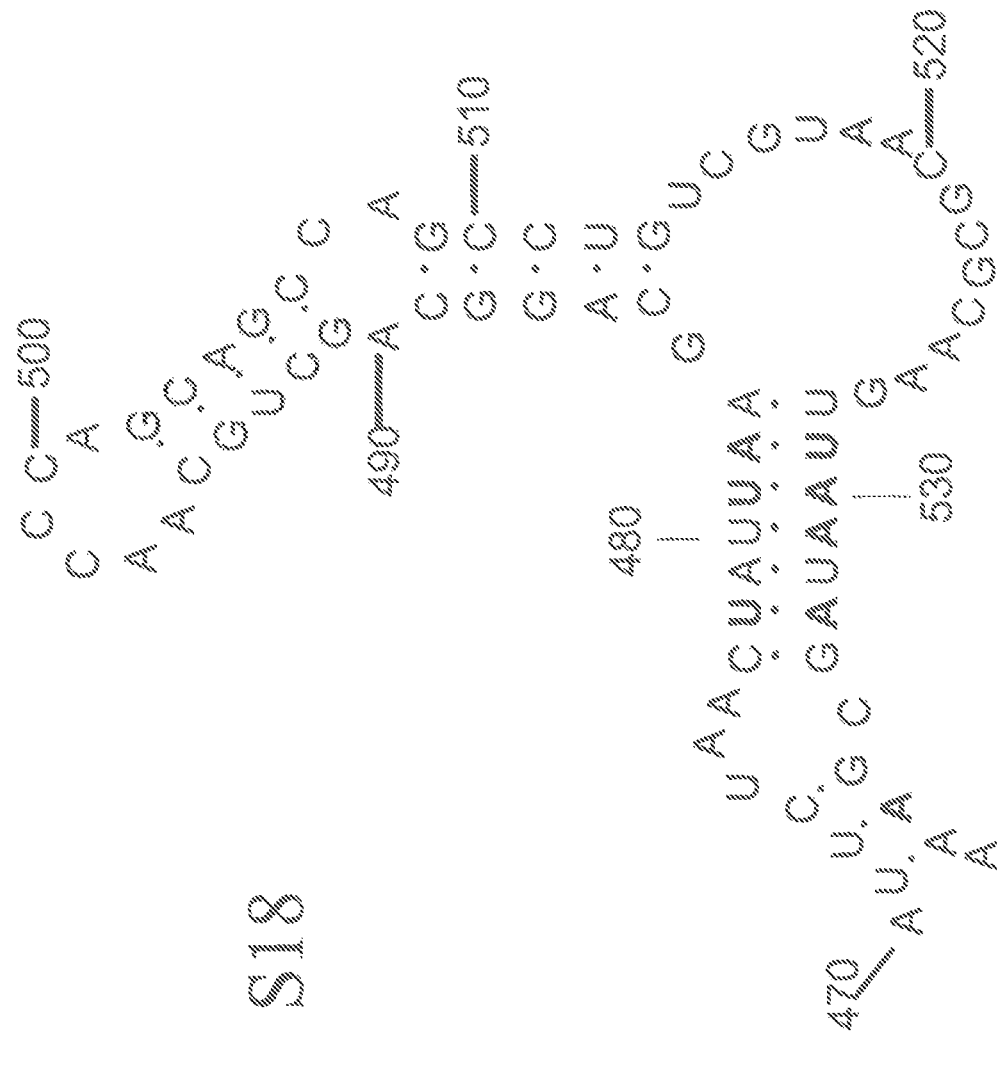
FIG. 5 shows the predicted RNA secondary structure of domain V (nucleotides 471-538) of the attenuated strain of the invention designated S18 (SEQ ID NO: 4).
Figure 6:
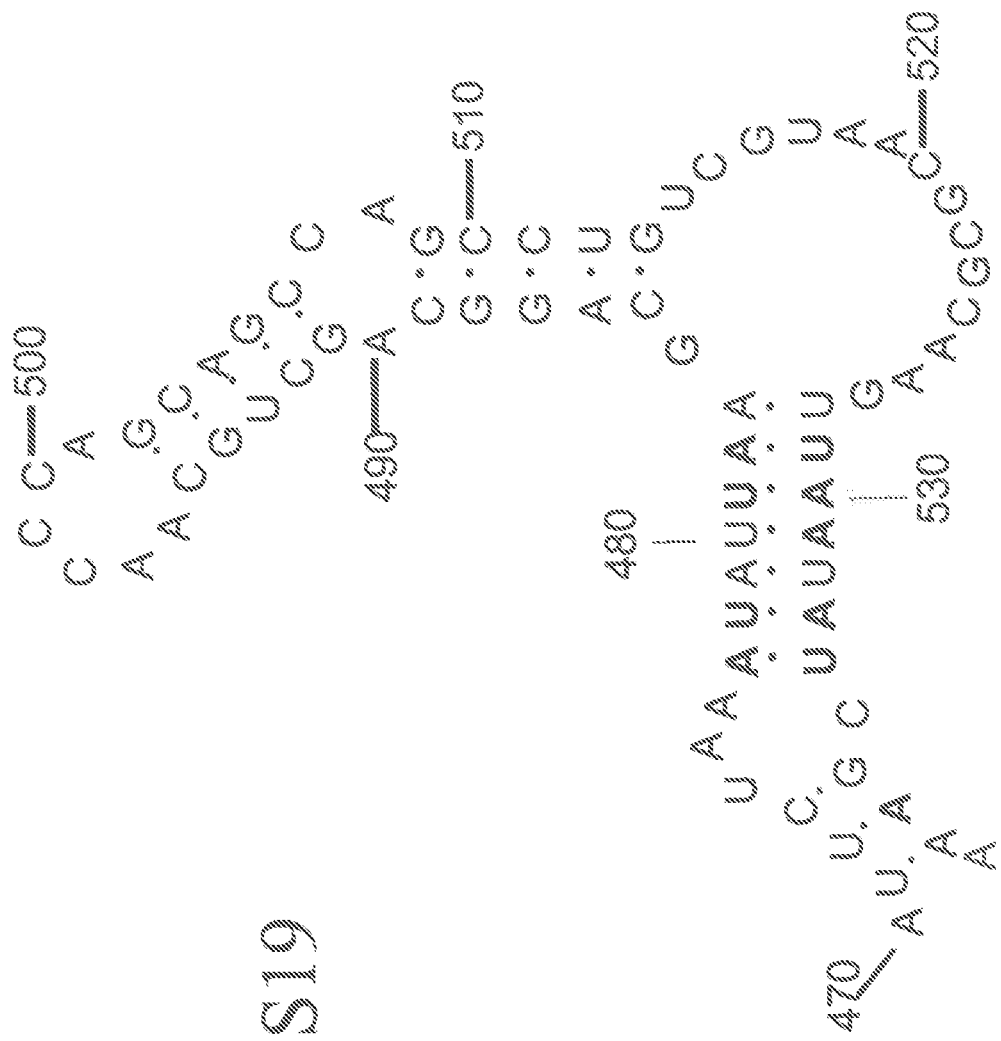
FIG. 6 shows the predicted RNA secondary structure of domain V (nucleotides 471-538) of the attenuated strain of the invention designated S19 (SEQ ID NO: 5).

Viruses were constructed and recovered by standard methods. More specifically, S17, S18 and S19 were constructed by PCR mutagenesis. For each plasmid, three fragments of the 5' non-coding region of Sabin 3 were amplified by PCR using primers incorporating the necessary sequence changes (as shown in FIGS. 4 to 6), located at nucleotides (a) 31-50 and 471-489, (b) 471-489 and 522-540 and (c) 522-540 and 755-778. The three overlapping fragments (a)-(c) were gel purified, mixed and re-amplified with outer primers then the 747 bp fragment comprising the mutated 5' non-coding region was cloned into pCR2.1 (Invitrogen) and sequenced. MluI-SacI (279-751) fragments with correct sequences were ligated into Sabin 3 clones lacking the SacI-SacI (751-1900) fragment. Full-length infectious clones were generated by addition of a partial SacI/SmaI (2768) fragment.

Under conditions which rapidly selected neurovirulent variants of Sabin 3, the attenuation phenotypes of poliovirus strain S15 and S16 were stable (WO98/41619). In order to generate genetically stable strains of all three serotypes the entire 5' non-coding region of Sabin 1 was replaced exactly with that of strain S15 to create S15/1 and the entire 5' non-coding region of Sabin 2 was replaced exactly with that of strain S15 to create S15/2.

More specifically, to make the S15/1, the 5' non-coding region of S15 was spliced precisely onto the coding region of Sabin 1 by PCR mutagenesis. The start of the coding region of the Sabin 1 clone pT7/S1F was amplified by PCR, digested with SacI and AatII, and gel purified. Plasmid pT7/S15 was digested with EcoRI and SacI, and the 0.78-kb fragment containing the T7 promoter and the first 751 nucleotides of the genome was gel purified. These fragments were ligated together into EcoRI-AatII-digested pT7/S1F to produce the full-length plasmid clone pT7/S15/1, which contained the entire 5' NCR of S15 and the coding region and 3' NCR of Sabin 1, as verified by sequencing of the first 1,200 nucleotides of the genome. As a consequence of the mutagenesis strategy, a silent T→A change was introduced into the second codon of the coding region of pT7/S15/1 compared to Sabin 1.

To make S15/2, the 5' non-coding region of T7/S15 was spliced precisely onto the coding region of Sabin 2 by overlapping PCR. The 5' NCR of pT7/S15 and the start of the coding region of the Sabin 2 clone pS2 were amplified; the overlapping fragments were gel purified, mixed, and reamplified with outer primers NP7 and AM13; and the resulting fragments were digested with NotI and SacI, gel purified, and ligated into NotI-SacI-digested pS2 to produce the full-length plasmid clone pT7/S15/2, which contained the entire 5' NCR of S15 and the coding region and 3' NCR of Sabin 2, as verified by sequencing of the first 1,500 nucleotides of the genome. Other than the exchanged 5' non-coding region, no mutations were introduced into the Sabin 2 sequence.

Two further S18 strains comprising sequences from the poliovaccine strains Sabin 1 (S18/1) and Sabin 2 (S18/2) were also constructed. S18/1 was generated by swapping the 0.78 kb EcoRI-SacI fragment of S18, containing the T7 promoter and the first 751 nucleotides of the genome, into S15/1. S18/1 comprises the 5' non-coding region of S18 spliced precisely onto the coding and 3' non-coding regions of Sabin 1. To make S18/2 the MluI-BamHI (674) fragment of S18 was swapped into a sub-clone of S15/2 then the full-length clone was generated using unique MluI and SacI (1318) sites in S15/2. S18/2 comprises the 5' non-coding region of S18 spliced precisely onto the coding and 3' non-coding regions of Sabin 2.

Viruses were recovered by transfection of HEp2C monolayers with ≥2 μg T7 transcripts (Van der Werf et al., Proc. Natl. Acad. Sci. USA 83:2330-2334, 1986) followed by incubation at 33° C. for 24-48 hours, by which time complete cytopathic effect was apparent. Sequences of 5' non-coding regions of all mutants were confirmed following RNA extraction and RT-PCR.

Temperature Sensitivity

We have previously shown that for genetically defined poliovirus strains that differ only in RNA domain V of the 5' non-coding region, temperature-sensitivity of growth is quantitatively related to the predicted stability of the folded RNA (Macadam et al., Virology 189:415-22, 1992).

Figure 7:
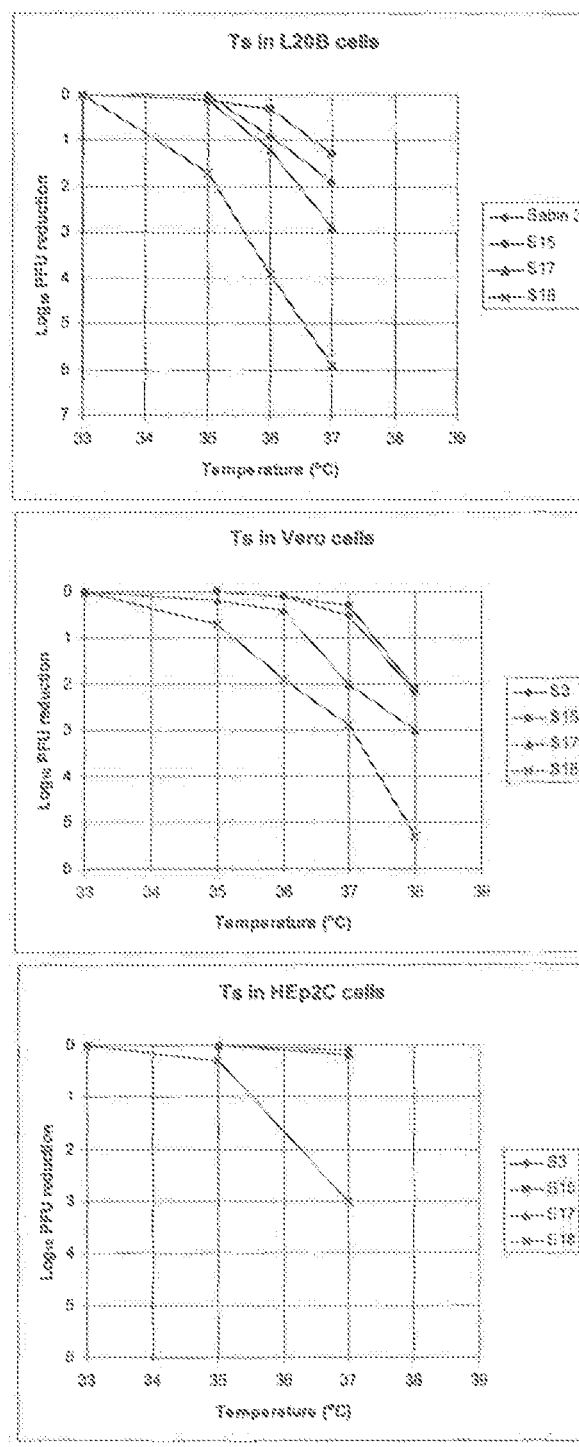
FIG. 7 shows the results of temperature sensitivity tests using poliovirus strains, Sabin 3, S15, S17 and S18. The reduction in number of plaques compared to the number of plaques at 33° C. is shown as a function of temperature, when grown in L20B, Vero and Hep2C cells.

Temperature-sensitivity assays were carried out using L20B, Hep2C and Vero cells as described in the above publication. Briefly, viruses were assayed by plaque-formation at different temperatures. These were controlled by incubation of inoculated cell culture plates in sealed plastic boxes submerged in water baths whose temperatures fluctuated by <0.01° C. Graphs in FIG. 7 show curves representing reduction in numbers of plaques compared to 33° C. as a function of temperature in three different cell lines.

Results show that weakening of domain V RNA secondary structure has a significant impact on the ability of the virus to replicate at human body temperature in all cell lines tested. In L20B cells there was no evidence of replication at all of S18 at 37° C. even using inocula containing 5×10$^5$ infectious units.

One-Step Growth Curves

Figure 8:
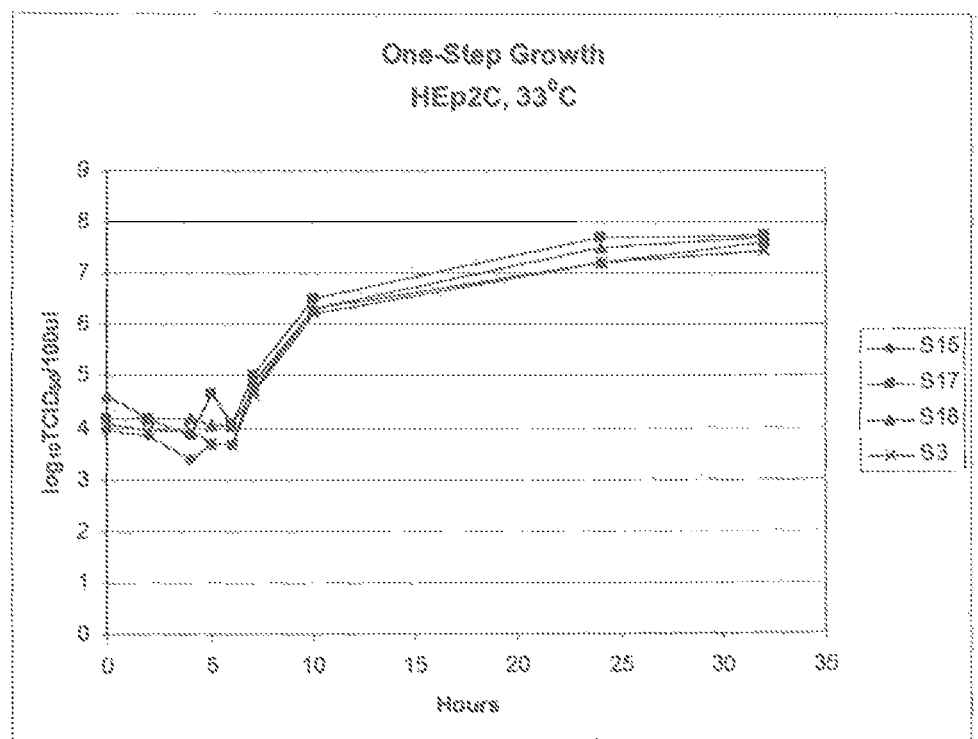
FIG. 8 shows the one step growth curves of Sabin 3 (S3), S15, S17 and S18 when grown on HEp2C cells at 33° C. $TCID_{50}$: tissue culture infectious dose 50%.

Replicate HEp2C cell sheets were infected synchronously with the different viruses at a multiplicity of infection of 10, incubated at 33° C. for different periods then harvested by freezing at −70° C. Virus titres in cell lysates were determined by standard methods (at 33° C.). Replication kinetics and virus yields were not significantly different for any of the viruses. The results are shown in FIG. 8.

Attenuation Phenotypes

Over the last 15 years the use of transgenic mice expressing the human poliovirus receptor to assess virulence of polioviruses has been established and validated.

Intraspinal inoculation of transgenic mice expressing the poliovirus receptor (TgPVR mice) is a highly sensitive method of measuring infectivity in vivo since virus replication leads to neuronal loss and obvious clinical signs of paralysis. Fewer than ten PFU of wild type viruses is usually sufficient to paralyse 50% of the mice using this route of inoculation (Chumakov et al., Dev. Biol. (Basel) 105:171-177, 2001). Here we made use the Tg66-CBA strain of mice, which is particularly sensitive to type 3 strains, to assess the infectivity of viruses S15, S17, S18 and S19.

Sabin 3, S15, S17 and S18 viruses were assayed by two routes of differing sensitivity, the intramuscular route and the intraspinal route. Initial results using these viruses are shown in Table 1. Both sets of initial experiments showed that S17 and S18 were more attenuated (less virulent) than the current type 3 vaccine strain and S15. S18 appeared completely attenuated, causing no clinical symptoms at all when inoculated intraspinally into the mice at a dose more than 3,000× higher than the PD$_{50}$ of Sabin 3.

Further tests using Sabin 1, Sabin 2, Sabin 3, 515, 517, 518, 519, S18/1 and S18/2 were carried out using the intraspinal route. The results of these tests are shown in Table 2. Strain S15 was indistinguishable from Sabin 3 in these tests (Table 1). Results for strain S17 showed that one extra C-G to U-A base-pair exchange increased the PD$_{50}$ more than 3000-fold. Strains S18 and S19 have one and two more C-G to U-A (or A-U) exchanges compared to S17 and appeared completely attenuated even at doses nearly 100.000-fold higher than the PD$_{50}$ of Sabin 3.

The PD$_{50}$ of S18/1 was more than a million-fold higher than that of Sabin 1 (Table 2), simply as a result of the 5' non-coding region exchange. The data for S18/1 are consistent with two extra C-G to U-A base-pair exchanges increasing PD$_{50}$ values by more than 10$^6$-fold.

Sabin 2 is the most attenuated of the three oral poliovaccine strains and has a relatively high PD$_{50}$ in TgPVR mice (Dragunsky et al., Bull. World Health Organ. 81:251-60, 2003). The PD$_{50}$ of S18/2 by the intraspinal route was even higher than that of Sabin 2 in Tg66-CBA mice (Table 2). Data for strains S18 and S18/1 suggests it would be several orders of magnitude higher than 10$^{8.1}$ but it was impractical to generate a virus preparation of high enough titre to test this.

Genetically Stable Strains of all Three Poliovirus Serotypes

Figure 10:
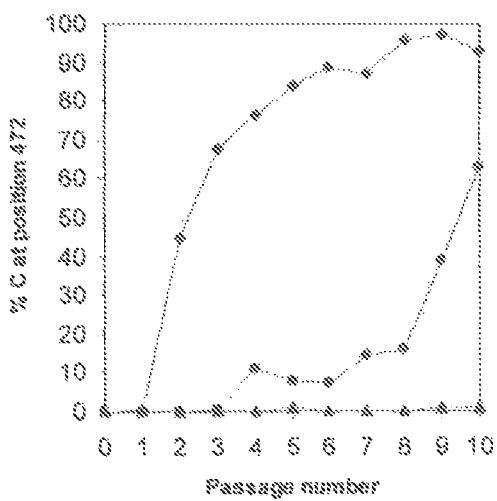
FIG. 10 shows the stability of 472 U in Sabin 3 on passage in different cell lines. Sabin 3 was passaged ten times in different cells at 37° C. 472 C content was then measured by PCR and restriction endonuclease digestion (MAPREC). Symbols ♦, L20B cells; ●, Vero cells: ▲ MRC-5 cells. L20B cells are mouse L cells expressing the human poliovirus receptor. Vero cells are used for vaccine production.

The stabilities of the S15/1 and S15/2 strains were compared with those of the relevant Sabin strains in the same way as for strain S15 using cell culture models which favored rapid reversion at attenuating nucleotides (FIG. 10).

Figure 9:
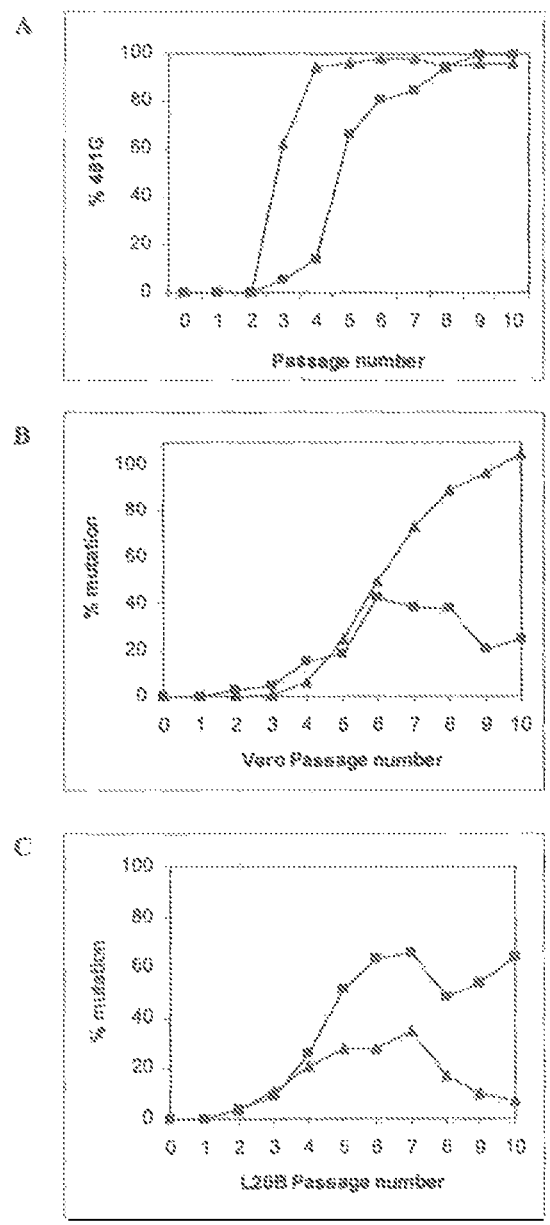
FIG. 9 shows the stability of attenuating mutations in domain V of Sabin 2 and Sabin 1 on passage in different cell lines. Viruses were passaged ten times in different cells at 37° C. then mutant proportions were measured by PCR and restriction endonuclease digestion (MAPREC). (A) Mutation at nucleotide 481 in Sabin 2 during passage in L20B cells (▲) and Vero cells (■). (B) Mutation in Sabin 1 during passage in Vero cells at nucleotides 480 or 525 (▲) and at nucleotide 476 (■). (C) Mutation in Sabin 1 during passage in L20B cells at nucleotides 480 or 525 (▲) and at nucleotide 476 (■).

The major attenuating mutation in the 5' non-coding region of Sabin 2 is an A at nucleotide 481 (equivalent to nucleotide 484 in FIG. 1) and an A to G mutation at this position, which results in significant loss of attenuation, was rapidly selected during passage of Sabin 2 in both L20B cells and Vero cells at 37° C. (FIG. 9A). By the third passage in L20B cells over 60% of the Sabin 2 population had a G at nucleotide 481 and after four passages selection was almost complete. In Vero cells over 60% of the Sabin 2 population had a G at nucleotide 481 after five passages and selection was essentially complete after 8-9 passages. No nucleotide changes were observed in domain V of strain S15/2 after ten passages in either L20B cells or Vero cells.

Three different mutations in domain V of Sabin 1 are selected during replication in the human gut, all of which strengthen base-pairing: 480 G to A, 525 U to C and 476 U to A (see FIG. 2). Nucleotides 480 and 525 form a base-pair so mutations occur at one or other position in a virus but not both. In Vero cells mutations at all three positions were selected in Sabin 1 at a steady rate (FIG. 9B) so that after six passages half of the virus population had a mutation at either 480 or 525 and more than 40% of the virus population had a mutation at 476. During the last four passages the proportion of the virus population that had a mutation at either 480 or 525 increased to approximately 100%, mainly due to mutation at nucleotide 480. Mutations at all three positions were also selected in Sabin 1 during passage in L20B cells (FIG. 9C), although, in contrast to results in Vero cells, mutations at 476 were selected at a higher rate than those at 480 and 525 so that after six passages approximately 60% of the virus population had a mutation at nucleotide 476 and 30% had a mutation at either 480 or 525. No nucleotide changes were observed in domain V of strain S15/1 after ten passages in either L20B cells or Vero cells.

TABLE 1

Attenuation/neurovirulence phenotypes in TgPVR mice
Log$_{10}$ PD$_{50}$ values in TgPVR mice

|  | i.m. | i.s. |
|---|---|---|
| Sabin 3 | 9.65 | 3.6 |
| S15 | 8.9 | n.d. |
| S17 | >9.3 (0/8)[1] | >7.1 (1/8) |
| S18 | >9.4 (0/8) | >7.1 (0/8) | i.m. intramuscular route
i.s. intraspinal route
n.d. not determined
PD$_{50}$ paralytic dose (50%)
[1] (proportion of mice paralysed at maximum dose)

TABLE 2

Attenuation/neurovirulence phenotypes in TgPVR mice

| Virus | PD$_{50}$ i.s./log$_{10}$ CCID$_{50}$ |
|---|---|
| Sabin 1 | 2.25 |
| S18/1 | >8.6 (1/16)* |
| Sabin 2 | 6.4 |
| S18/2 | >8.1 (0/8)* |
| Sabin 3 | 3.6 |
| S15 | 3.7 |
| S17 | >7.1 (4/16)* |
| S18 | >8.4 (0/16)* |
| S19 | >8.2 (0/16)* | i.m. intramuscular route
PD$_{50}$ paralytic dose (50%)
*paralysed/total at highest dose While illustrative embodiments have been illustrated and described, it will be appreciated that various changes can be made therein without departing from the spirit and scope of the invention.

The embodiments of the invention in which an exclusive property or privilege is claimed are defined as follows:

1. A method of vaccinating a human patient against poliomyelitis, comprising administering to said patient an immunogenic composition comprising an effective amount of an inactivated or attenuated poliovirus vaccine which does not have a base pair mismatch in stem (a) or (b) of domain V of the 5' non-coding region of its genome, wherein at least seven of the base pairs in stems (a) and (b) are U-A or A-U base pairs and a pharmaceutically acceptable carrier or diluent.

2. The method according to claim 1, wherein at least five of the base pairs in stem (b) of the 5' non-coding region of the poliovirus genome are U-A or A-U base pairs.

3. The method according to claim 1, wherein six of the base pairs in stem (b) of the 5' non-coding region of the poliovirus genome are U-A or A-U base pairs.

4. The method according to claim 1, wherein seven of the base pairs in stem (b) of the 5' non-coding region of the poliovirus genome are U-A or A-U base pairs.

5. The method according to claim 1, wherein two of the base pairs in stem (a) of the 5' non-coding region of the poliovirus genome are U-A or A-U base pairs.

6. The method according to claim 1, wherein three of the base pairs in stem (a) of the 5' non-coding region of the poliovirus genome are U-A or A-U base pairs.

7. The method according to claim 1, wherein said poliovirus comprises domain V of the 5' non-coding region of poliovirus type 3 in which a U-A base pair is present at position 472-537 in stem (a) and at positions 478-533, 480-531 and 481-530 in stem (b).

8. The method according to claim 7, in which an A-U base pair is present at position 482-529 in stem (b) of the 5' non-coding region of the poliovirus genome.

9. The method according to claim 7, in which an A-U base pair is present at position 477-534 in stem (b) of the 5' non-coding region of the poliovirus genome.

10. The method according to claim 1, wherein the poliovirus is inactivated by formaldehyde treatment.

\* \* \* \* \*

SEQUENCE LISTING

<160> NUMBER OF SEQ ID NOS: 5

<210> SEQ ID NO 1
<211> LENGTH: 70
<212> TYPE: DNA
<213> ORGANISM: Artificial Sequence
<220> FEATURE:
<223> OTHER INFORMATION: domain V of polio virus strain Sabin 3

<400> SEQUENCE: 1 auucuaaccauggagcaggc agcugcaacc cagcagccag ccugucguaa cgcgcaaguc    60
cguggcggaa                                                          70

<210> SEQ ID NO 2
<211> LENGTH: 70
<212> TYPE: DNA
<213> ORGANISM: Artificial Sequence
<220> FEATURE:
<223> OTHER INFORMATION: modified domain V of polio virus strain Sabin
      3 - S15

<400> SEQUENCE: 2 auucuaaccauugagcaggc agcugcaacc cagcagccag ccugucguaa cgcgcaaguc    60
aauggcgaaa                                                          70

<210> SEQ ID NO 3
<211> LENGTH: 70
<212> TYPE: DNA
<213> ORGANISM: Artificial Sequence
<220> FEATURE:
<223> OTHER INFORMATION: modified domain V of polio virus strain Sabin
      3 - S17

<400> SEQUENCE: 3 auucuaacuauugagcaggc agcugcaacc cagcagccag ccugucguaa cgcgcaaguc    60
aauagcgaaa                                                          70

<210> SEQ ID NO 4
<211> LENGTH: 70
<212> TYPE: DNA
<213> ORGANISM: Artificial Sequence
<220> FEATURE:
<223> OTHER INFORMATION: modified domain V of polio virus strain Sabin
      3 - S18

<400> SEQUENCE: 4 auucuaacuauuaagcaggc agcugcaacc cagcagccag ccugucguaa cgcgcaaguu    60
aauagcgaaa                                                          70

<210> SEQ ID NO 5
<211> LENGTH: 70
<212> TYPE: DNA
<213> ORGANISM: Artificial Sequence
<220> FEATURE:
<223> OTHER INFORMATION: modified domain V of polio virus strain Sabin
      3 - S19

<400> SEQUENCE: 5 auucuaaauauuaagcaggc agcugcaacc cagcagccag ccugucguaa cgcgcaaguu    60
aauaucgaaa                                                          70